United States Patent [19]

Celmer et al.

[11] 4,225,674

[45] Sep. 30, 1980

[54] PROCESS FOR PRODUCING NEW ANSAMYCIN ANTIBIOTIC

[75] Inventors: Walter D. Celmer, New London; Walter P. Cullen, East Lyme; John R. Oscarson, Pawcatuck; Liang H. Huang, East Lyme, all of Conn.; Riichiro Shibakawa, Handa; Junsuke Tone, Aichi, both of Japan

[73] Assignee: Pfizer Inc., New York, N.Y.

[21] Appl. No.: 34,408

[22] Filed: Apr. 30, 1979

[51] Int. Cl.² ............................................. C12P 17/12
[52] U.S. Cl. .................................. 435/122; 435/886; 260/239.3 T
[58] Field of Search ......................................... 435/122

[56] References Cited

U.S. PATENT DOCUMENTS

| | | | |
|---|---|---|---|
| 3,094,461 | 6/1963 | Prokop | 435/128 |
| 3,116,202 | 12/1963 | Dietz et al. | 435/886 |
| 3,880,858 | 4/1975 | Oshida et al. | 435/122 |

OTHER PUBLICATIONS

Handbook of Microbiology, vol. III, CRC Press, p. 202, (1973).

*Primary Examiner*—Alvin E. Tanenholtz
*Attorney, Agent, or Firm*—Connolly and Hutz

[57] ABSTRACT

A new subspecies of *Streptomyces nigellus* Prokop, designated *Streptomyces nigellus* Prokop subsp. *africanus* Huang subsp. nov. ATCC 31496, when propagated under aerobic conditions in aqueous nutrient media, produces a mixture of antibiotics. One of these antibiotics is the known macrolide antibiotic cirramycin A; the ansamycin antibiotic is an analogue of protostreptovaricin and the structure has been established as 21-hydroxy, 25-demethyl, 25-methylthioprotostreptovaricin I.

1 Claim, 1 Drawing Figure

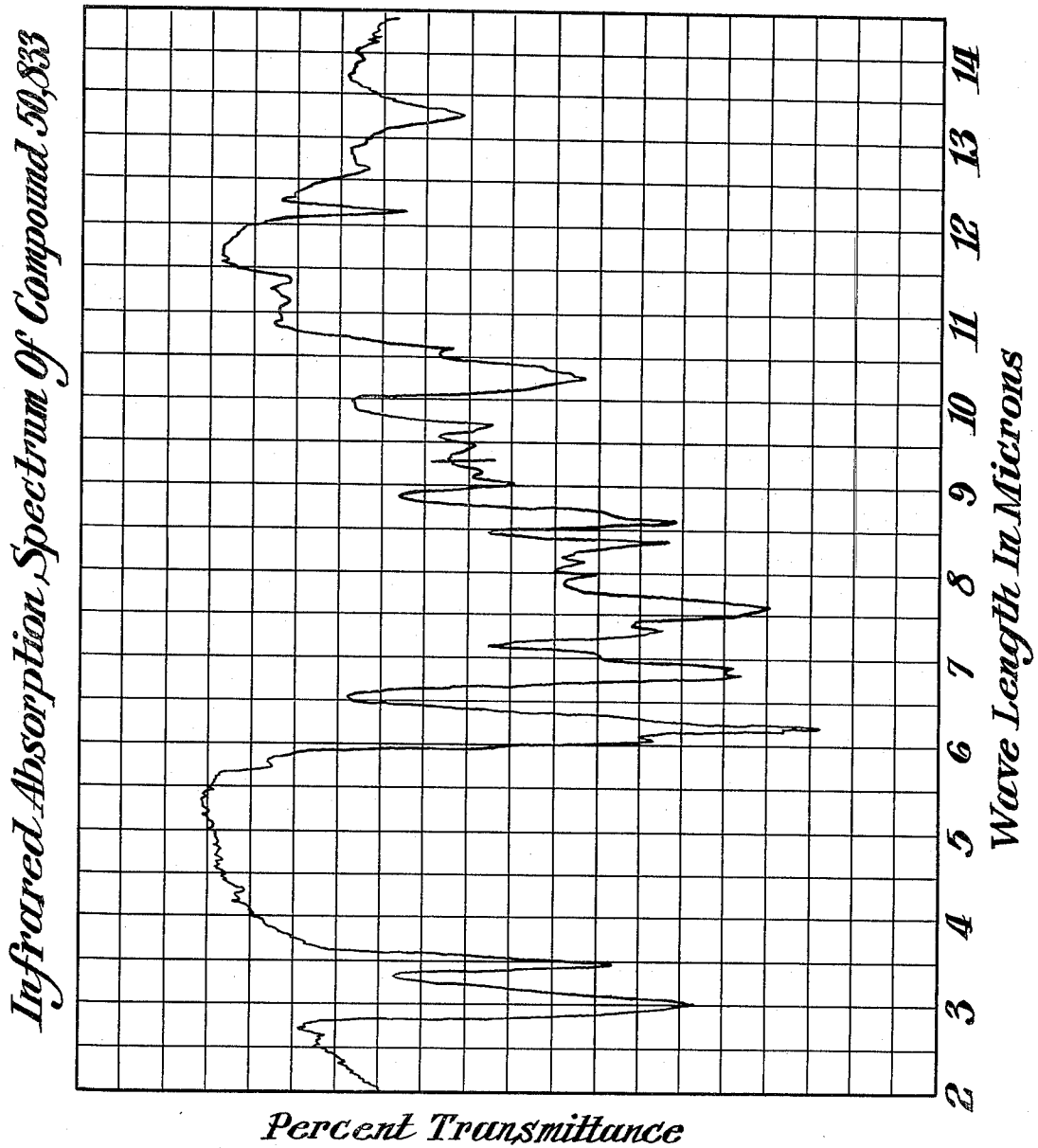

PROCESS FOR PRODUCING NEW ANSAMYCIN ANTIBIOTIC

BACKGROUND OF THE INVENTION

Large molecule lactone antibiotics are often referred to as macrolide antibiotics. Well known members of this class of antibiotics include erythromycin and oleandomycin.

The ansamycins constitute a class of antibiotics characterized by an aliphatic bridge linking two non-adjacent positions of an aromatic nucleus. The rifamycins and streptovaricins are well known members of this class of antibiotics. The chemistry of the ansamycin antibiotics is reviewed by K. L. Rinehart, Jr. and L. S. Shield in Progress in the Chemistry of Organic Natural Products, published by Springer-Verlag, Vienna - New York (1976).

Summary of the Invention

*Streptomyces nigellus* Prokop subsp. *africanus* Huang subsp. nov. ATCC 31496, when propagated under aerobic conditions in aqueous nutrient media, produces known macrolide antibiotic cirramycin A and a new ansamycin established as 21-hydroxy, 25-demethyl, 25-methylthioprotostreptovaricin I.

Detailed Description of the Invention

The microorganism useful for the preparation of the antibiotics of this invention was isolated from a soil sample from Egypt. This culture, designated as *Streptomyces nigellus* Prokop subsp. *africanus* Huang subsp. nov., has been deposited in The American Type Culture Collection, Rockville, MD. as the type culture under their accession number ATCC 31496. The permanency of the deposit of this culture at The American Type Culture Collection at Rockville, Maryland and ready accessibility thereto by the public are afforded throughout the effective life of the patent in the event the patent is granted. Access to the culture is available during pendency of the application under 37 CFR 1.14 and 35 USC 112. All restrictions on the availability to the public of the culture deposited will be irrevocably removed upon granting of the patent.

The culture was planted from a slant into liquid ATCC No. 172 medium and grown for 3 days at 28° C. on a shaker. It was then removed from the shaker, centrifuged for 20 minutes, washed three times with sterile distilled water and planted on media commonly used for identification of members of the Actinomycetales.

The inoculated plates were incubated at 28° C. and records of results were made after suitable incubation time with most of the final results recorded at 15 days. The colors were described in common terminology, but exact color was determined by comparison with color chips from the Color Harmony Manual, fourth edition. The method of whole-cell analysis is that described by Becker, B. et al., Appl. Microbiol., 12, 421–423 (1964).

Identification media used for the characterization of the culture and references for their composition are as follows:

1. Tryptone Yeast Extract Broth—(ISP #1 medium, Difco).
2. Yeast Extract-Malt Extract Agar—(ISP #2 medium, Difco).
3. Oatmeal Agar—(ISP #3 medium, Difco).
4. Inorganic Salts-Starch Agar—(ISP #4 medium, Difco).
5. Glycerol-Asparagine Agar—(ISP #5 medium, Difco).
6. Peptone-Yeast Extract Iron Agar—(ISP #6 medium, Difco).
7. Tyrosine Agar—(ISP #7 medium, Difco).
8. Czapek-Sucrose Agar—S. A. Waksman, The Actinomycetes, Vol. 2, medium no. 1, p. 328, 1961.
9. Glucose Asparagine Agar—Ibid, medium no. 2, p. 328.
10. Bennett's Agar—Ibid, medium no. 30, p. 331.
11. Emerson's Agar—Ibid, medium no. 28, p. 331.
12. Nutrient Agar—Ibid, medium no. 14, p. 330.
13. Gordon and Smith's Tyrosine Agar—R. E. Gordon and M. M. Smith, Jr. Bact. 69:147–150, 1955.
14. Casein Agar—Ibid.
15. Calcium Malate Agar—S. A. Waksman, Bact. Rev. 21:1–29, 1957.
16. Gelatin—R. E. Gordon and J. M. Mihm, Jr. Bact. 73:15–27, 1957.
17. Starch—Ibid.
18. Organic Nitrate Broth—Ibid.
19. Dextrose Nitrate Broth—S. A. Waksman, The Actinomycetes, Vol. 2, medium no. 1, p. 328, 1961 with 3 g dextrose substituted for 30 g sucrose and agar omitted.
20. Potato Carrot Agar—M. P. Lechevalier, Jr. Lab. and Clinical Med. 71:934–944, 1968 but use only 30 g potatoes, 2.5 g carrots and 20 g agar.
21. 2% Tap Water Agar.
22. Skim Milk—Difco.
23. Cellulose utilization—
   (a) H. L. Jensen, Proc. Linn. Soc. N.S.W. 55:231–248, 1930.
   (b) M. Levine and H. W. Schoenlein, A Compilation of Culture Media, medium no. 2511, 1930.
24. Carbohydrates—ISP #9 medium, Difco.
25. Temperature Range—ATCC medium 172 in ATCC Culture Collection Catalogue, 12th ed. p. 329, 1976.

The culture was described as follows on the various culture media:

Yeast Extract-Malt Extract Agar—Growth good, dark greyish (near grey series 2 fe to 2 ih), slightly raised, wrinkled, with greyish aerial mycelium; reverse brown to dark brown (3 ng to 3 ni); soluble pigment pale yellowish brown.

Oatmeal Agar—Growth moderate, pale greyish to grey (near grey series 2 dc to 2 fe), occurring as small isolated colonies, thin, velvet, spreading near the edge, with pale grey to grey aerial mycelium; reverse pale greyish (Near grey series 2 dc); no soluble pigment.

Inorganic Salts-Starch Agar—Growth good, greyish (near grey series 2 fe), slightly raised and wrinkled, with grey aerial mycelium; reverse pale yellowish brown (2 1c); no soluble pigment.

Glycerol-Asparagine Agar—Growth poor, greyish (near grey series 2 fe), occurring as small isolated dots, aerial mycelium grey; reverse same as surface; no soluble pigment.

Gordon and Smith' Tyrosine Agar—Growth good, greyish (near grey series 2 fe), thin to slightly raised, smooth but slightly wrinkled near the edge, aerial mycelium grey; reverse greyish brown (3 ie); no soluble pigment.

Czapek-Sucrose Agar—Growth moderate to good, dark greyish (near grey series 2 ih), mixed with greyish dots, velvet to floccose, with grey to dark grey aerial mycelium; reverse greyish (near grey series 2 fe); no soluble pigment.

Glucose Asparagine Agar—Growth poor to moderate, white to pale yellowish (1½ ca), occurring as small, isolated dots which were smooth to wrinkled, slightly raised to raised, aerial mycelium, if present, white to pale yellowish; reverse pale yellowish (1½ ea); no soluble pigment.

Calcium Malate Agar—Growth moderate, dark grey (near grey series 2 ih), velvet, occurring as small isolated dots, with dark grey aerial mycelium; reverse same as surface; no soluble pigment.

Casein Agar—Growth moderate, cream (1½ ca), raised, wrinkled, aerial mycelium absent, reverse same as surface; with yellowish brown soluble pigment (2 1c).

Bennett's Agar—Growth good, dark grey (near grey series 2 ih) with a few small white dots, raised, wrinkled, aerial mycelium dark grey; reverse greyish brown (2 ie to 2 1g); no soluble pigment.

Emerson's Agar—Growth good, white to pale greyish (near grey series 2 dc), raised, wrinkled, with white to grey aerial mycelium; reverse pale yellowish (1½ ca); soluble pigment yellowish brown (3 ne).

Nutrient Agar—Growth moderate to good, grey (near grey series 2 fe), slightly raised and roughened, with grey aerial mycelium; reverse same as surface; no soluble pigment.

Gelatin Agar—Growth good, pale greyish (near grey series, between 2 dc and 2 fe), slightly raised, smooth but wrinkled near the edge, with pale grey aerial mycelium; reverse colorless; no soluble pigment.

Starch Agar—Growth good, greyish (near grey series, between 2 fe and 2 ih), slightly raised, smooth but wrinkled near the edge, with grey aerial mycelium; reverse colorless to cream; no soluble pigment.

Potato Carrot Agar—Growth moderate, dark grey (near grey series 2 ih), velvet, occurring as small, isolated dots, with dark grey aerial mycelium; reverse same as surface; no soluble pigment.

Tap Water Agar—Growth poor, dark grey (near grey series 2 ih), velvet, occurring as very small, isolated dots, with dark grey aerial mycelium; reverse same as surface; no soluble pigment.

Biochemical Properties—Melanin not produced; hydrogen sulfide produced; gelatin liquefied; starch hydrolyzed; nitrate not reduced to nitrite on both media; good growth but no decomposition on both cellulose media; clearing but no peptonization and no coabulation on milk; casein digestion negative; digestion of calcium malate positive; tyrosine digestion positive. Carbohydrate utilization: glucose, arabinose, fructose, inositol, mannitol, raffinose, rhamnose, sucrose and xylose all utilized.

Temperature Relations—

| 21° C. | 28° | 37° | 45° |
|---|---|---|---|
| good growth | good growth | moderate growth | no growth |

Morphological Properties—Spore chains in Section Spirales or RA, 10 to 30 spores per chain, but may be less than 10, in hooks, loops, irregular or incomplete spirals, or spirals of one to three turns which were open, and might be irregularly arranged or enclosed in a droplet. This spore chain morphology was seen on oatmeal agar and inorganic salts-starch agar. On yeast extract-malt extract agar and glycerol asparagine agar the spore chains were straight, flexuous, hooked or looped. The following morphological observations were made on the 15-day-old culture grown on oatmeal agar: sporophores monopodailly or sometimes verticillately branched, spores smooth to warty, oval to elliptical, 1.2–2×1–1.2 μm.

Cell Wall Analysis—The culture is characterized by the presence of LL-diaminopimelic acid in the cell wall, grey aerial mycelium, S or RA spore chain morphology, smooth to warty spores and melanin-negative reaction. It closely resembles *Streptomyces nigellus* Prokop described in U.S. Pat. No. 3,094,461, and thus the type strain of *S. nigellus* NRRL 2920 was used for comparison. The characteristics they share in common include color of aerial mycelium, spore chain morphology, melanin reaction, positive gelatin liquefaction, negative nitrate reduction, inability to coagulate and peptonize milk, positive digestion of calcium malate, and the pattern of carbohydrate utilization. The new culture differs from *S. nigellus* NRRL 2920 in positive starch hydrolysis, presence of some warty spores besides the smooth ones, and absence of some globose spores. Some minor differences in cultural characteristics were observed. *S. nigellus* NRRL 2920 differs on yeast extract-malt extract agar in having grey aerial mycelium with pale pinkish tint, a colorless to pale grey colony reverse, and no soluble pigment; on inorganic salts-starch agar *S. nigellus* NRRL 2920 grows as thin colonies with grey reverse. Based on the above similarities and differences, the culture is considered to be a new subspecies of *S. nigellus*, and is designated as *Streptomyces nigellus* Prokop subsp. *africanus* Huang subsp. nov.

Cultivation of *Streptomyces nigellus* subsp. *africanus* ATCC 31496 preferably takes place in aqueous nutrient media at a temperature of 24°–36° C. and under submerged aerobic conditions with agitation. Nutrient media which are useful for such purposes include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles and yeast extract as well as salts such as sodium chloride and calcium carbonate and trace elements such as iron, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about 178 to 2 volumes of free air per volume of broth per minute. Agitation may be maintained by means of agitators generally familiar to those in the fermentation industry. Aseptic conditions must, of course, be maintained through the transfer of the organism and throughout its growth.

Inoculum for the preparation of the antibiotic may be obtained by employing growth from a slant of the culture. The growth may be used to inoculate either shake flasks or inoculum tanks or the inoculum tanks may be seeded from the shake flasks. Growth in shaken flasks will generally have reached its maximum in 2 to 4 days whereas inoculum in submerged inoculum tanks will usually be at the most favorable period in 1.5–3 days. Substantial antibiotic activity is obtained in the final fermentor stage in approximately 2 to 5 days.

The process of antibiotic production is conveniently followed during fermentation by biological assay of the broth employing a sensitive strain of *Staphylococcus aureus* or *Micrococcus luteus*. Standard plate assay technique is employed in which the zone of inhibition surrounding a filter paper disc saturated with broth is used as a measure of antibiotic potency.

Thin-layer chromatography employing silica gel is a useful tool for analyzing the antibiotics produced by *Streptomyces nigellus* subsp. africanus ATCC 31496 in fermentation media and the composition of crude and purified materials extracted from fermentation broths. Silica gel plates are employed with a developing system of chloroform-methanol(3:1 or 9:1 v/v). These antibiotics may be visualized by exposure to 254 nm light or bio-overlay with a thin layer of agar seeded with a sensitive strain of *Staphylococcus aureus* or *Micrococcus luteus*.

The antibiotics may be separated and recovered by extracting the whole, unfiltered fermentation broth with an organic solvent, such as chloroform, ethyl acetate, methylisobutyl ketone or butanol at a pH range of 4.0 to 10. The solvent is concentrated to a thin syrup, defatted with heptane, the residue partitioned between a pH 5 phosphate buffer and chloroform and the solvent layer containing Compound 50,833 chromatographed on silica gel.

A method of separation and purification of antibiotic Compound 50,833 is as follows: Whole fermentation broth is extracted with several volumes of methylisobutyl ketone. The solvent extract is then concentrated in vacuo. The concentrated extract is stirred with heptane. After separation, the heptane phase is washed with methanol. The methanol is filtered and evaporated in vacuo and combined with the heptane insoluble phase which is also filtered and evaporated in vacuo.

The combined concentrate is passed through a column packed with a hydroxypropyl dextran gel (Sephadex LH-20, Pharmacia Fine Chemicals, Piscataway, New Jersey) in methanol. Column cuts are examined by thin-layer chromatography on silica gel plates developed with chloroform-methanol (9:1). Cuts containing orange pigmented Compound 50,833 are combined, evaporated and re-chromatographed on Sephadex LH-20. The purified material is then chromatographed on a column packed with silica gel slurried in ethyl acetate. Heart cuts from the column developed with ethyl acetate are combined, concentrated in vacuo and washed with 5% sodium phosphate monobasic buffer adjusted to pH 4.0 with phosphoric acid. The solvent phase is separated, washed with water and evaporated in vacuo. The residue is dissolved in a small volume of chloroform and Compound 50,833 precipitated as an orange colored solid by the rapid addition of heptane.

The present invention includes within its scope the dilute forms and crude concentrates of the mixture of antibiotics and the purified antibiotic Compound 50,833. All of these compositions are useful in combating microorganisms, especially strains of *Staphylococcus aureus* that are resistant to other antibiotics.

Table I illustrates the antibacterial spectrum of Compound 50,833. These tests were run by preparing tubes of nutrient broth with gradually increasing concentrations of the pure antibiotic and then seeding the broths with the particular organism specified. The minimal inhibitory concentration indicated in Table I is the minimal concentration of the antibiotic (in micrograms/ml) at which the microorganisms failed to grow. The tests were conducted under standardized conditions as described in Proc. Soc. Exp. Biol. & Med., 122, 1107 (1966).

TABLE I

| Organism | Compound 50,833 (mcg/ml) |
|---|---|
| *Staphylococcus aureus* | |
| 01A005 | 0.39 |
| 01A052 | 0.39 |
| 01A109 | 0.20 |
| 01A110 | 0.20 |
| 01A400 | 0.39 |
| *Staphylococcus epidermidis* | |
| 01B087 | 0.78 |
| 01B111 | >100 |
| 01B126 | 0.78 |
| *Streptococcus faecalis* | |
| 02A006 | 50 |
| *Streptococcus agalactiae* | |
| 02B006 | >100 |
| *Streptococcus pyogenes* | |
| 02C000 | >100 |
| 02C203 | >100 |
| *Pseudomonas aeruginosa* | |
| 52A104 | >100 |
| *Klebsiella pneumoniae* | |
| 53A009 | >100 |
| 53A031 | >100 |
| *Salmonella typhimurium* | |
| 58D009 | >100 |
| *Pasteurella multocida* | |
| 59A001 | >100 |
| *Enterobacter aerogenes* | |
| 67A040 | >100 |
| *Escherichia coli* | |
| 51A266 | >100 |
| 51A470 | 1.56 |

In vivo protection is afforded by Compound 50,833 against mice experimentally infected with *Staphylococcus aureus* 01A005 (a strain sensitive to most of the commercially available antibiotics) with an oral $PD_{50}$ of about 33 and a subcutaneous $PD_{50}$ of about 14.

Antibiotic Compound 50,833 can be administered via the oral or parenteral routes for the treatment in animals, including humans, of staphylococcal and other antibiotic-sensitive infections. In general, the antibiotic is most desirably administered in daily oral doses of 0.5 to 1 gram of parenteral injections of 100 to 500 mg., depending on the type and severity of the infection and weight of the subject being treated.

Antibiotic Compound 50,833 may be administered alone or in combination with pharmaceutically-acceptable carriers, and such administration can be carried out in both single and multiple doses.

For purposes of oral administration, tablets containing various excipients such as sodium citrate, calcium carbonate and dicalcium phosphate may be employed along with various disintegrants such as starch, alginic acid and certain complex silicates together with binding agents such as polyvinylpyrrolidone, sucrose, gelatin and gum acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials include lactose as well as high molecular weight polyethylene glycols. When aqueous suspensions and/or elixirs are desired for oral administration, the essential active ingredient therein may be combined with various sweetening or flavoring agents, coloring matter or dyes, and if desired, emulsifying and/or suspending agents as well, together with such diluents as water, ethanol, propylene glycol, glycerol and various combinations thereof.

For purpose of parenteral administration, solutions of Compound 50,833 or solutions of a mixture of the antibiotics produced by *Streptomyces nigellus* subsp. *africanus* ATCC 31496 in sesame or peanut oil or in aqueous propylene glycol may be employed.

EXAMPLE I

A sterile aqueous medium having the following composition was prepared:

| Ingredient | Grams/liter |
| --- | --- |
| Glucose | 10 |
| Soluble starch | 20 |
| Yeast extract | 5 |
| Enzymatic digest of casein | 5 |
| Dipotassium hydrogen phosphate | 0.5 |
| Meat meal | 5 |
| Cobalt chloride | 0.002 |
| Calcium carbonate | 4 |
| pH 7.1–7.2 | |

Cells from a slant culture of *Streptomyces nigellus* subsp. *africanus* ATCC 31496 were transferred to each of a number of 300 ml shake flasks each containing 40 ml of the above medium and shaken at 28° C. for three to four days.

A sterils aqueous medium having the following composition was prepared:

| Ingredient | Grams/liter |
| --- | --- |
| Glucose | 10.0 |
| Casein | 5.0 |
| Starch | 5.0 |
| Corn steep liquor | 5.0 ml |
| Calcium carbonate | 3.0 |
| Cobalt chloride | 0.002 |
| pH 6.9–7.02 | |

Fermentors containing two liters of the above described sterile medium were seeded with 2–4% v/v of grown inoculum. The temperature was maintained at 30° C. The broth was stirred at 1700 r.p.m. and aerated at the rate of about one volume of air per volume of broth per minute. When substantial antibiotic activity was obtained (based on antibiotic disc assay), ca. 2–5 days, the filtered or whole fermentation broth was twice extracted with ⅓ to ½ volume of methylisobutyl ketone. The solvent was separated from the aqueous phase and concentrated in vacuo to a viscous oil.

EXAMPLE II

The fermentation process of Example I may be repeated employing the following fermentation medium:

| Ingredient | Grams/liter |
| --- | --- |
| Dextrin | 20 |
| Soybean flour | 10 |
| Distiller's solubles | 1 |
| Ferrous sulfate | 0.1 |
| pH 6.9–7.1 | |

EXAMPLE III

The fermentation process of Example I may be repeated employing the following fermentation medium:

| Ingredient | Grams/liter |
| --- | --- |
| Soy flour | 30 |
| Starch | 50 |
| Magnesium sulfate | 5 |
| Monopotassium hydrogen phosphate | 6 |
| Dipotassium hydrogen phosphate | 3.5 |
| pH 6.9–7.1 | |

EXAMPLE IV

A methylisobutyl ketone extract of 1200 gallons of the broth of Example I was concentrated in vacuo to approximately two liters, then stirred with eight liters of heptane. After separation, the heptane phase was washed with two liters of methanol. The methanol was filtered and evaporated in vacuo (100 grams) and combined with the heptane insoluble phase which was also filtered and evaporated in vacuo (63 grams).

The combined concentrate was passed in two runs (80 grams each) down a column packed with one liter of Sephadex LH-20 in methanol. The flow rate of the column was 50 ml/minute. The column was washed with methanol between runs. Cuts containing the orange pigmented Compound 50,833 from both runs were combined and evaporated (28 grams).

The 28 grams of crude material dissolved in ethyl acetate was applied to an 80 mm × 1 m column packed with column grade silica gel 60 (Merck) slurried in ethyl acetate. The column was developed with ethyl acetate at a rate of 60 ml/minute. Progress of the column was followed by silica gel thin-layer chromatography.

Heart cuts from the column were combined and evaporated to a volume of approximately one liter and then washed with one liter of 5% sodium phosphate monobasic buffer adjusted to pH 4.0 with 85% phosphoric acid. The separated solvent phase was washed with water and then evaporated in vacuo. Compound 50,833 was precipitated as an orange colored solid by dissolving the residue in 10 ml of chloroform and rapidly adding 200 ml of heptane. The solids (500 mg) were collected by filtration and dried 16 hours in vacuo at 50° C.

The filtrate was evaporated (5.2 grams) and chromatographed on a 2.5 × 100 cm column packed with silica gel 60 in ethyl acetate. The column was developed with ethyl acetate at the rate of 5 ml/minute with 20 cuts collected. The fractions containing Compound 50,833 were combined, washed with an equal volume of 5% sodium phosphate monobasic buffer (pH 4.5) and then with an equal volume of water. The solvent layer was evaporated in vacuo to dryness, the residue taken up in 5 ml of chloroform and Compound 50,833 precipitated by the rapid addition of 50 ml of heptane. The orange solids were collected by filtration and dried 16 hours in vacuo at 50° C. (yield 410 mg, m.p. 133°–150° C.).

A basic, white antibiotic isolated from the 5% sodium phosphate monobasic buffer solution (pH 4.0 to 4.5) was found to be the previously reported macrolide antibiotic cirramycin A, U.S. patent No. 3,159,540.

The weakly acidic, orange colored antibiotic component exhibits absorption maxima in 0.01 N methanolic NaOH at 237, 299 and 412 nm with $E_1^{1\%}$ cm values of 482, 301 and 123, respectively.

Elemental analyses calculated for a molecular weight of 685.5 and a molecular formula of a $C_{36}H_{47}O_{10}NS$.

When pelleted in KBr, Compound 50,833 exhibits characteristic absorption in the infrared region at the following wavelengths in microns as shown in the attached drawing: 3.05, 3.45, 6.22, 6.82, 6.90, 7.30, 7.60, 8.34, 8.57, 9.05, 9.72, 10.30, 12.20, and 13.32.

Mass spectrometer and nmr data are consistent with 21-hydroxy,25-demethyl,25-methylthioprotostreptovaricin I as shown in the following structural formula:

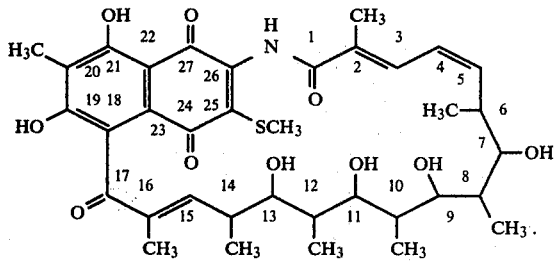

We claim:

1. A process for preparing an antibiotic mixture which comprises cultivating *Streptomyces nigellus* Prokop subsp. *africanus* Huang subsp. nov. ATCC 31496 in an aqueous nutrient medium containing an assimilable source of carbon and nitrogen until substantial antibiotic activity is obtained and separating said antibiotic mixture therefrom.

* * * * *